United States Patent [19]
Wack et al.

[11] Patent Number: 6,027,534
[45] Date of Patent: Feb. 22, 2000

[54] MODULAR ELBOW

[75] Inventors: Michael A. Wack, Warsaw, Ind.; Arnold-Peter C. Weiss, Barrington, R.I.; D. Steven Block, Warsaw, Ind.

[73] Assignee: DePuty Orthopaedics, Inc., Warsaw, Ind.

[21] Appl. No.: 08/963,138

[22] Filed: Nov. 3, 1997

[51] Int. Cl.[7] ............................................ A61F 2/38
[52] U.S. Cl. ................................. 623/20; 623/19; 623/21
[58] Field of Search .................................. 623/19, 20, 21

[56] References Cited

U.S. PATENT DOCUMENTS

| | | |
|---|---|---|
| 3,708,805 | 1/1973 | Scales et al. . |
| 3,939,496 | 2/1976 | Ling et al. . |
| 4,057,858 | 11/1977 | Helfet . |
| 4,079,469 | 3/1978 | Wadsworth . |
| 4,106,128 | 8/1978 | Greenwald et al. . |
| 4,136,405 | 1/1979 | Pastrick et al. ................. 623/20 |
| 4,193,139 | 3/1980 | Walker ........................... 623/21 |
| 4,224,695 | 9/1980 | Grundei et al. . |
| 4,242,758 | 1/1981 | Amis et al. . |
| 4,261,064 | 4/1981 | Helfet . |
| 4,280,231 | 7/1981 | Swanson . |
| 4,293,963 | 10/1981 | Gold et al. . |
| 4,301,552 | 11/1981 | London . |
| 4,462,120 | 7/1984 | Rambert et al. . |
| 4,538,306 | 9/1985 | Dörre et al. . |
| 4,822,366 | 4/1989 | Bolesky . |
| 4,923,472 | 5/1990 | Ugolini . |
| 4,936,853 | 6/1990 | Fabian et al. . |
| 4,950,298 | 8/1990 | Gustilo et al. . |
| 4,985,037 | 1/1991 | Petersen . |
| 5,030,237 | 7/1991 | Sorbie et al. . |
| 5,194,066 | 3/1993 | Van Zile . |
| 5,330,534 | 7/1994 | Herrington et al. . |
| 5,376,121 | 12/1994 | Huene et al. . |
| 5,755,804 | 5/1998 | Schmotzer et al. ............... 623/20 |
| 5,879,390 | 3/1999 | Kubein-Meesenburg et al. ....... 623/18 |

OTHER PUBLICATIONS

Article entitled "Passive Motion of the Elbow Joint," The Journal of Bone and Joint Surgery, vol. 58–A, No. 4, Jun. 1976.

Leaflet entitled "The Cavedish Elbow,"Thackray® Orthopaedic, date unknown.

Advertising literature for The Capitello–Condylar Total Elbow, Johnson & Johnson Products, Inc. Orthopaedic Division, date unknown.

Two pages of material discussing prosthetic replacement of the elbow, author and date unknown.

Two pages of advertising literature, Souter Strathclyde™ Total Elbow System, Howmedica, date unknown.

Two pages of literature concerning nonconstrained metal of plastic total elbow replacement, author and date unknown.

"Operative Technique for the Capitello–Condylar Total Elbow Prosthesis," Frederick C. Ewald, M.D., date unknown.

One page of advertising literature, "All the right pieces for . . . Outstanding Performance," The Kudo Elbow, Biomet Ltd, date unknown.

*Primary Examiner*—Paul B. Prebilic

[57] ABSTRACT

A modular elbow prothesis includes a humeral component, an ulnar component and three bearing components. The ulnar component includes a stem for implantation in the intramedullary canal of an ulna and a body including a slot. Two of the three bearing components include flanges that mate with the slot of the ulnar component. The humeral component includes a stem for implantation in the intramedullary canal of the humerus and two arms extending from one end of the stem. An opening is formed in each arm and in two of the three bearing components. The modular elbow may be used in an unconstrained mode by attaching one bearing component to the ulnar component and the other to the humeral component by inserting a pin through the openings in the arms and the bearing component. The two bearing components are then placed adjacent each other such that they articulate about their bearing surfaces. Alternatively, the prosthesis can be utilized in a constrained mode by positioning the flange of the third bearing component in the slot on the ulnar component and positioning the third bearing component between the arms of the humeral component and inserting a pin through the openings in the arms of the third component.

33 Claims, 3 Drawing Sheets

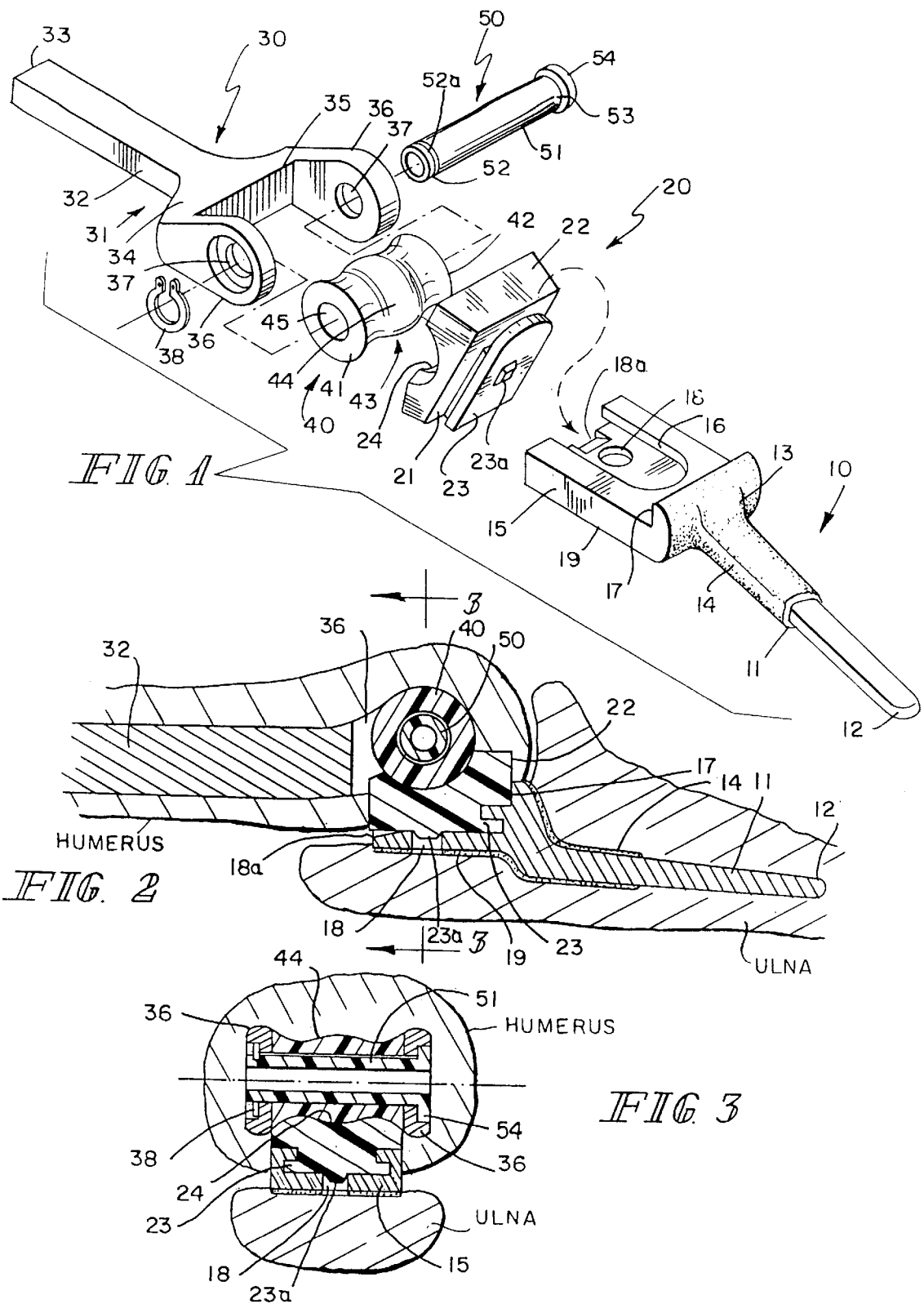

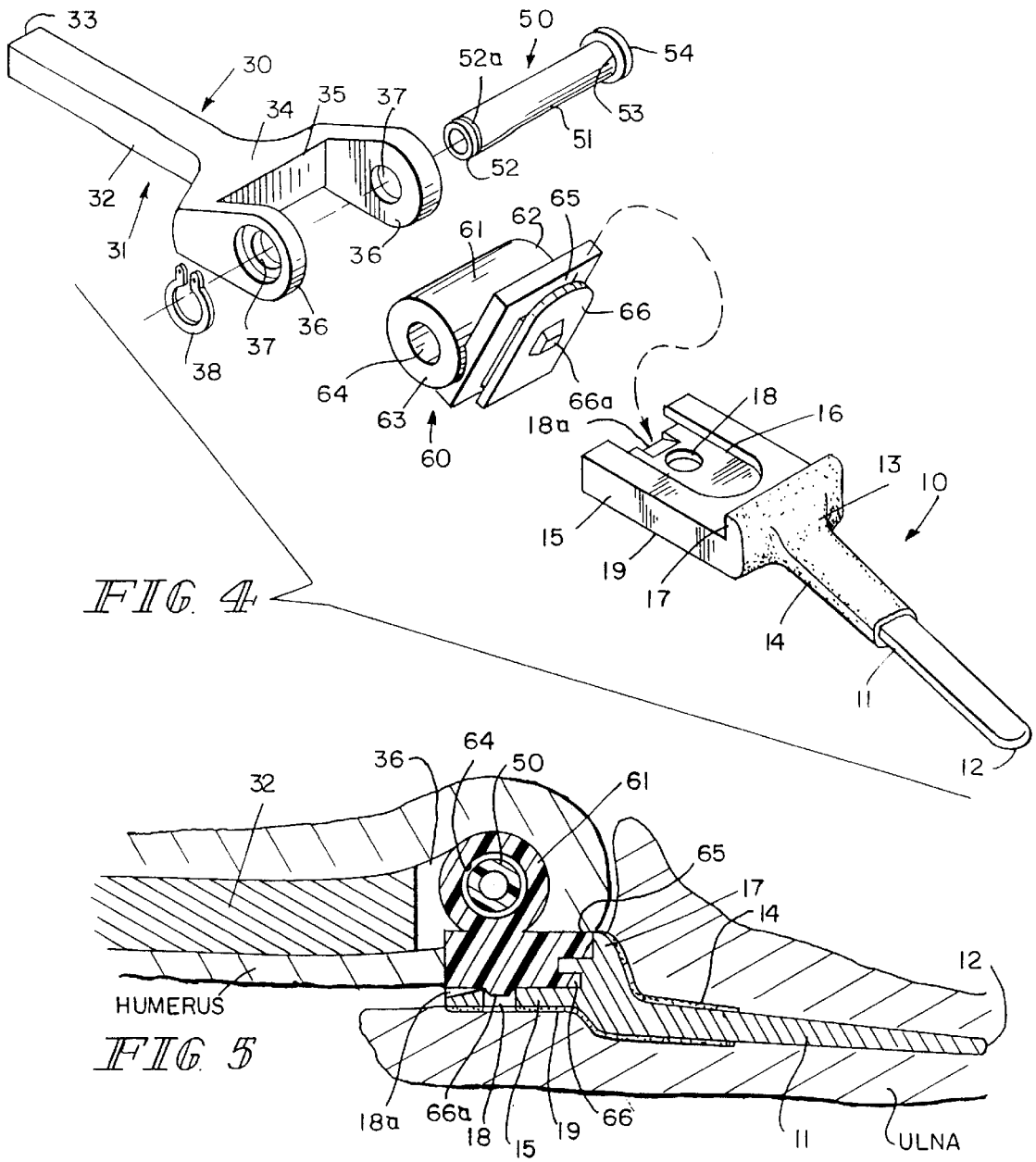

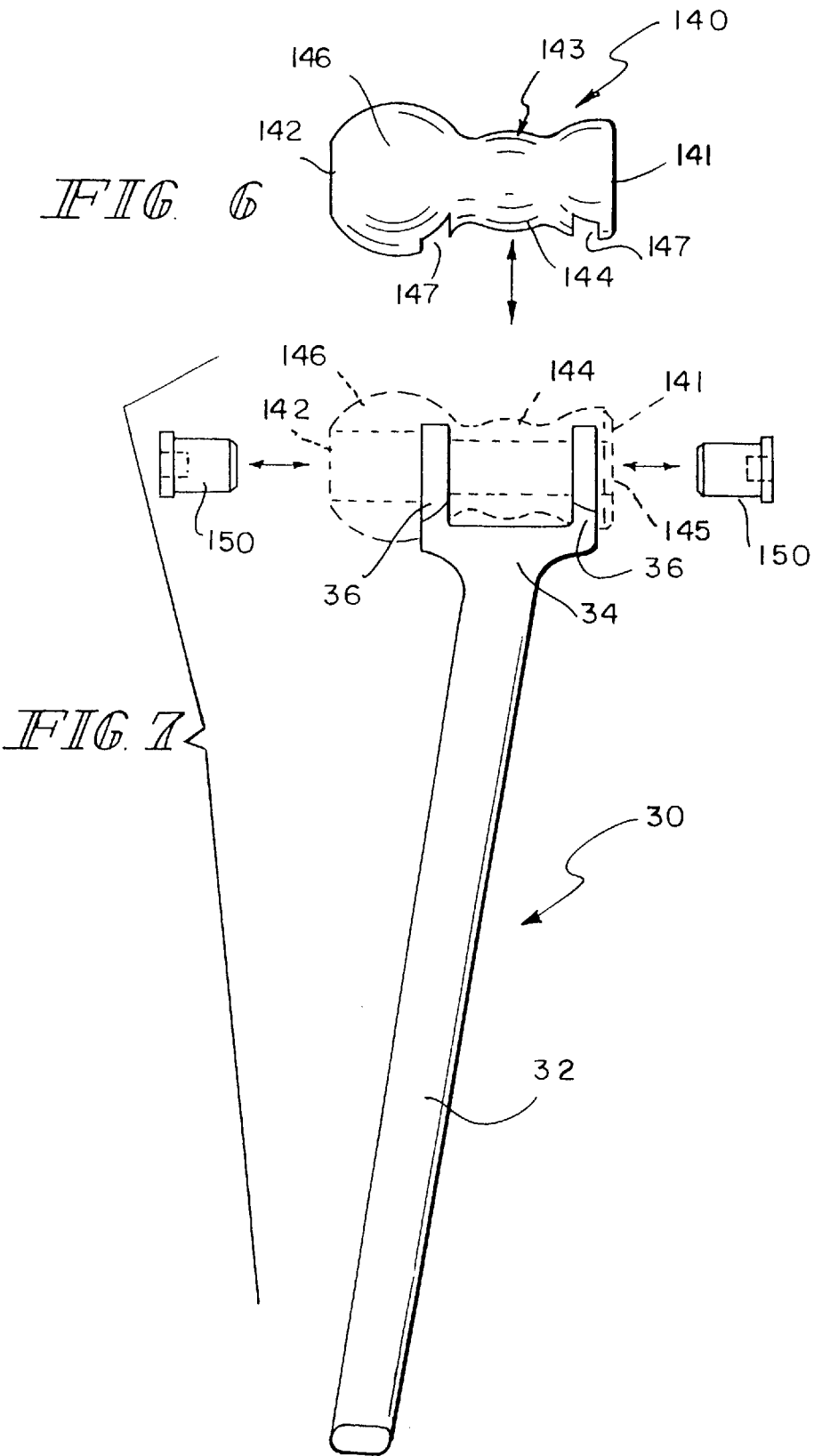

MODULAR ELBOW

BACKGROUND AND SUMMARY OF THE INVENTION

The present invention relates to artificial joints and, in particular, to a modular elbow prosthesis.

Two basic types of elbow prosthesis are known in the prior art: constrained and unconstrained. In constrained prosthesis, the prosthetic joint is held together mechanically, by components of the prosthesis. Such devices are shown, for example, in U.S. Pat. No. 5,376,121 to Huene et al., U.S. Pat. No. 3,708,805 to Scales, et al., U.S. Pat. No. 3,939,496 to Ling, et al., and U.S. Pat. No. 4,224, 695 to Grundei, et al. In an unconstrained device, the prosthetic device is held together by the patient's natural soft tissues. Such a device is shown in U.S. Pat. No. 4,293,963 to Gold, et al. In each of these devices, one portion of the prosthesis is implanted in the humerus of the patient and the other portion is implanted in the ulna. The two portions then mate in some manner to allow articulation of the joint. In the '695 patent to Grundei, et al., an additional portion of the prosthesis is implanted in the radius of the patient.

A surgeon may not always know prior to beginning an operation whether a patient would be better served by a constrained or unconstrained elbow prosthesis. Thus, it would be desirable to provide an elbow prosthesis that may be utilized in either the constrained or unconstrained manner.

It may also be necessary to convert an unconstrained elbow prosthesis to a constrained one, or vice versa, after implantation and use for a period of time. In order to do so, it is typically necessary to remove the portion of the prosthesis implanted in the humerus and ulna and to replace the entire prosthesis with either the constrained or unconstrained variety.

The present invention provides an elbow prosthesis that can be utilized in either a constrained or unconstrained fashion. The elbow prosthesis of the present invention can be converted from a constrained to an unconstrained prosthesis and from an unconstrained to a constrained prosthesis after implantation in a patient's body.

These features are attained by the provision of a modular prosthetic joint having a first stem, a second stem and three bearing components. The first stem has a first end and a second end and a body connected to it. A slot is formed in the body. The first bearing component has a flange configured to mate with the slot. A pair of arms extend from one end of the second stem. The second bearing component is adapted to fit between the arms of the second stem and configured to mate with the bearing surface of the first bearing component. The third bearing component is interchangeable with the first and second bearing components and is adapted to fit between the arms of the second stem. The third bearing component also includes a flange configured to mate with the slot.

According to one embodiment of the invention, the prosthesis includes an opening in each of the arms, an opening in the second bearing component and a pin adapted to extend through the openings in the arms and second bearing component.

In another embodiment, the prosthesis includes an opening in each of the arms, an opening in the third bearing component and a pin adapted to extend through the openings in the arms and the third bearing component.

In one embodiment of the invention, the bearing surface of the first bearing component is concave and the second bearing component includes a convex surface.

According to another embodiment of the invention, a modular prosthetic elbow includes an ulnar component having a stem with a first end adapted to fit within the medullary canal of a human ulna and a second end, a humeral component having a stem with a first end adapted to fit within the medullary canal of a human humerus, a first bearing component adapted to engage the ulnar component, a second bearing component adapted to engage the humeral component and mate with the first bearing component so as to be held in place by the soft tissues of the elbow, and a third bearing component interchangeable with the first and second bearing components, the third bearing component adapted to engage the ulnar component and be held in place by the humeral component.

In one embodiment, the ulnar component includes a slot and the first bearing component includes a flange configured to mate with the slot. The humeral component includes a pair of arms and the second bearing component is adapted to fit between the arms. An opening is formed in each of the arms and in the second bearing component and a pin is adapted to extend through the openings in the arms and the second bearing component.

In one embodiment, the humeral component includes a pair of arms and the third bearing component is adapted to fit between the arms. An opening is formed in each of the arms and in the third bearing component. A pin is adapted to extend through the openings in the arms and the third bearing component.

In another embodiment, a slot is formed in the ulnar component and a flange is connected to the third bearing component and configured to engage the slot. In another embodiment, a slot is formed in the ulnar component, a flange is connected to the first bearing component and configured to engage the slot, and another flange is formed on the third bearing component and configured to engage the slot.

In another embodiment of the invention, a prosthetic modular elbow includes an ulnar component having a proximal end and a distal end and a humeral component having a proximal end and a distal end. A first bearing mount is formed on the humeral component for engagement with at least two of a plurality of bearing components. A second bearing mount is located on the ulnar component for engagement with at least two of a plurality of bearing components. In one embodiment, the first bearing mount includes a pair of spaced apart arms extending from the humeral component. The arms may be located at the distal end of the humeral component. In another embodiment of the invention, the second bearing mount is located at the proximal end of the ulnar component and may include a slot formed in a portion of the ulnar component. In one embodiment of the invention, the first and second bearing mounts are configured to simultaneously engage one of the plurality of bearing components.

According to another embodiment of the present invention, a modular elbow prosthesis includes a humeral component with a bearing mount and an ulnar component with a bearing mount. First and second bearing components are configured to engage the humeral and ulnar bearing mounts respectively so as to form an unconstrained prosthesis. A third bearing component, interchangeable with the first and second bearing components, is configured to engage the humeral and ulnar components so as to form a constrained prosthetic elbow. The humeral bearing mount may include a pair of spaced apart arms. The ulnar bearing mount may include a slot. The third bearing component may include a cylindrical body with an opening therein and may have a flange attached thereto. The flange is configured to mate with the ulnar bearing mount. The first bearing component may include a flange configured to mate with the ulnar bearing mount. The second bearing component may include an opening.

In another embodiment of the present invention, a modular prosthetic elbow includes a humeral component, an ulnar component, a first bearing for joining the humeral and ulnar components to form a constrained prosthetic elbow and a set of bearings interchangeable with the first bearing for providing pivotal movement of the ulnar component relative to the humeral component in an unconstrained manner.

A method according to the present invention includes the steps of implanting a first component of a prosthesis in the ulna, implanting a second component of the prosthesis in the humerus and selecting from a group of three bearing components two bearing components, one to be joined to the first component of the prosthesis and a second to be joined to the second component of the prosthesis, or selecting the remaining bearing component and securing it to the first and second components of the prosthesis.

In one embodiment, the method further comprises the step of joining the first two bearing components to the first and second components so as to form an unconstrained prosthetic elbow. In another embodiment, the method further includes the step of joining the third bearing component to the first and second component so as to form a constrained prosthetic elbow.

Other objects, advantages and novel features of the present invention will become apparent from the following detailed description of the preferred embodiments and the accompanying drawings.

BRIEF DESCRIPTION OF THE DRAWINGS

FIG. 1 is an exploded perspective view of a modular elbow according to the present invention for use in the unconstrained configuration.

FIG. 2 is a longitudinal cross-sectional view showing the modular elbow of FIG. 1 implanted in the arm of a person.

FIG. 3 is a cross-sectional view taken along line 3—3 in FIG. 2.

FIG. 4 is an exploded perspective view of the modular elbow according to the present invention for use in the constrained mode.

FIG. 5 is a longitudinal cross-sectional view showing the modular elbow of FIG. 4 implanted in the arm of a person.

FIG. 6 is a plan view of an alternative second bearing component that forms a component of a modular elbow according to the present invention.

FIG. 7 is a plan view of the bearing component of FIG. 6 attached to a humeral component that is a component of modular elbow according to the present invention.

DETAILED DESCRIPTION OF THE DRAWINGS

FIG. 1 is an exploded perspective view of a modular elbow according to the present invention for use in the unconstrained mode. The modular elbow prothesis comprises ulnar component 10, first bearing component 20, humeral component 30, second bearing component 40, and pin 50.

Ulnar component 10 comprises a stem 11 having a first or distal end 12 and a second or proximal end 13. A portion of stem 11 adjacent second end 13 may be coated with a material 14 to allow bone ingrowth between the stem and ulna. Any of various known bone ingrowth coatings, such as cobalt-chromium or titanium alloys, may be used. A generally rectangular body 15 is secured to second end 13 and has a slot 16 formed therein. Body 15 and slot 16 form a mount for a plurality of bearing components, as described below. Stem 11 extends from body 15 at an angle thereto. A raised stop member 17 is formed at the juncture of stem 11 and body 15. An opening 18 is formed in body 15 and is configured to receive a nubbin on first bearing component 20 or third bearing component 60, as described below. Body 15 further includes a sloped, recessed area or notch 18a utilized for guiding the nubbin into opening 18, as described below. Ulnar component 10 can be made from any surgical alloy, such as cobalt-chrome or titanium. Portions of ulnar component 10 other than or in addition to stem 11 may include a bone ingrowth coating. For example, bone ingrowth coating may be applied to underside 19 of body 15.

First bearing component 20 generally comprises a base 21 with a stop member 22 extending therefrom at a generally ninety degree angle. A flange 23 is formed on base 21 and is configured to mate with slot 16 in body 15 of ulnar component 10, as described below. A nubbin 23a extends from flange 23. Bearing component 20 further includes a concave bearing surface 24. Bearing surface 24 mates with second bearing component 40 as described below, when the modular elbow prosthesis is used in the unconstrained mode.

Humeral component 30 includes a stem 31 having a first segment 32 with a first or proximal end 33 and a second segment 34 with a second or distal end 35. Second segment 34 is integral with first segment 32 and widens with distance from first end 33. A pair of spaced apart arms 36 extend from second end 35 at an angle to second segment 34 of stem 31. Each arm 36 includes an opening 37. Arms 36 and openings 37 form a mount for a plurality of bearing components, as described below. A locking ring 38 is disposed about one opening 37. Humeral component 30 may also be made of a surgical alloy, such as cobalt-chrome.

Second bearing component 40 is a generally cylindrical member that flares outward at first end 41 and second end 42. Middle segment 43 of second bearing component 40 has a convex outer surface 44. The outer surface of second bearing component 40 mates with bearing surface 24 of first bearing component 20 when the modular elbow prosthesis is used in the unconstrained mode, as described below. Second bearing component 40 also includes a central opening or bore 45.

Pin 50 is a generally cylindrical member having a main body portion 51, a first end 52 and a second end 53. First end 52 includes a slot 52a to engage with locking ring 38 and secure pin 50 in place. Second end 53 includes an enlarged head or flange 54. Head 54 has a larger diameter than openings 37 in arms 36 of humeral component 30. A central opening or bore 55 extends through pin 50.

To use the elbow prosthesis of the present invention in the unconstrained mode (FIGS. 2 and 3), ulnar component 10 is implanted in an ulna such that stem 11 is located in the intramedullary canal as shown in FIG. 2. In a similar fashion, humeral component 30 is inserted in the humerus such that stem 31 is located in the intramedullary canal as shown in FIG. 2. Ulnar component 10 and humeral component 30 can be fixed to the ulna and humerus, respectively, with or without bone cement. First bearing component 20 is positioned such that flange 23 is adjacent slot 16 in body 15 of ulnar component 10. First bearing component 20 is then slid toward stop member 17. As this occurs, locking nubbin 23a engages notch 18a. As first bearing component 20 is moved into further engagement with ulnar component 10, locking nubbin 23a rides upward along notch 18a and is compressed by it. When first bearing component 20 is fully seated in ulnar component 10, locking nubbin 23a is located over opening 18a and decompresses. Locking nubbin 23a thus extends into opening 18a and prevents first bearing component 20 from pulling back out of slot 16 in body 15. Second bearing component 40 is positioned between arms 36 of humeral component 30 such that opening 45 is aligned with opening 37. Pin 50 is then inserted through an opening 37 in one arm 36, through opening 45 in second bearing component 40 and through the remaining opening 37 in the other arm 36 such that locking ring 38 engages slot 52a. Second bearing component 40 is then placed adjacent first bearing component 20 such that their concave and convex surfaces mate. First and second bearing components 20 are held in position by the soft tissues of the elbow. In this manner, bearing components 20 and 40 articulate about their bearing surfaces and permit movement of the lower arm.

FIG. 4 shows an exploded perspective view of the components of the modular elbow prosthesis of the present invention for use in the constrained mode. In this mode, ulnar component 10, humeral component 30 and pin 50 of the unconstrained configuration are utilized in conjunction with a third bearing component 60. Third bearing component 60 includes a generally cylindrical member 61 having a first end 62, a second end 63 and a bore or opening 64 extending therethrough. Cylindrical member 61 is connected to base 65. A flange 66 is connected to base 65 opposite cylindrical body 61. Flange 66 is configured to mate with slot 16 of body 15 in the same way as previously described for first bearing component 20. A locking nubbin 66a is formed on flange 66. First bearing component 20, second bearing component 40 and third bearing component 60 may all be made from surgical metal or plastic, such as ultra-high molecular weight polyethylene.

To implant the modular elbow of the present invention in the constrained mode, ulnar component 10 is implanted in the ulna such that stem 11 is located in the intramedullary canal as shown in FIG. 5. Similarly, stem 31 of humeral component 30 is positioned in the intramedullary canal of the humerus as shown. Third bearing component 60 is then secured to body 15 of ulnar component 10 by sliding flange 66 in groove 16 of body 15 until locking nubbin 66a engages opening 18. Cylindrical body 61 of third bearing component 60 is then positioned between arms 36 of humeral component 30 such that opening 64 is aligned with openings 37 in arms 36. Pin 50 is then inserted through one opening 37 in an arm 36, through opening 64 in third bearing component 60 and through opening 37 in the remaining arm 36 such that locking ring 38 engages slot 52a. In this manner, third bearing component 60 can articulate about pin 50 between arms 36. Third bearing component 60 is held in place by pin 50 and arms 36, rather than the soft tissues of the elbow.

Thus, with the present invention, a modular prosthesis kit is provided that allows for intra-operative implantation of a constrained or unconstrained elbow prosthesis. Additionally, if it is necessary to convert an unconstrained prosthesis to a constrained configuration, with the present invention, the change can be made after implantation and without removing the ulnar and humeral components. To do so, the arm is surgically opened and pin 50 and second bearing component 40 are removed from arms 36 on the humeral component. First bearing component 20 is removed from ulnar component 10 by compressing locking nubbin 23a and sliding flange 23 out of slot 16. Third bearing component 60 is then secured to ulnar component 10 by inserting flange 66 into slot 16. Cylindrical body 61 is then positioned between arms 36 such that opening 64 is aligned with openings 37 in arms 36. A pin 50 is then inserted through the openings in arms 36 and third bearing component 60 and locked in place with lock ring 38. In this manner, a surgeon is provided with a modular elbow prosthesis kit that allows the surgeon to decide, after surgery has begun, whether to utilize a constrained or unconstrained prosthesis. Furthermore, the present invention provides a prosthesis that can be converted from a constrained to an unconstrained configuration, or vice versa, without removing the ulnar and humeral components from the patient.

FIGS. 6 and 7 show an alternative embodiment of the second bearing component attached to humeral component 30. Second bearing component 140 includes a generally cylindrical member having a first and 141 and a second and 142. The middle segment 143 of second bearing component 140 includes a convex outer surface 144. The outer surface of second bearing component 140 mates with bearing surface 24 of first bearing component 20 when the modular elbow prosthesis is used in the unconstrained mode. Bearing component 140 also includes a central opening or bore 145 extending therethrough. Adjacent second end 142 is an enlarged body or head 146. A pair of slots or openings 147 are formed in bearing component 140.

To secure bearing component 140 to humeral component 30, arms 36 are inserted into slots 147 such that openings 37 therein align with opening or bore 145 in bearing component 140. Openings 37 may be threaded to receive screws 150 to secure bearing component 140 to humeral component 30. Alternatively, a pin and locking ring arrangement, as described above, may be used. Additional methods of securing bearing component 140 to humeral component 30 may also be used.

Although the present invention has been shown and described in detail the same is to be taken by way of example only and not by way of limitation. Numerous changes can be made to the embodiments shown without departing from the scope of the invention. Accordingly, the invention is to be limited only by the terms of the claims appended hereto.

What is claimed is:

1. A prosthetic joint kit, comprising:
    a first stem having a first end and a second end;
    a body connected to the first stem;
    a slot formed in the body;
    a first bearing component having a bearing surface;
    a flange connected to the first bearing component and configured to mate with the slot;
    a second stem having a first end and a second end; a pair of arms extending from one end of the second stem;
    a second bearing component adapted to fit between the arms of the second stem and configured to mate with the bearing surface of the first bearing component;
    a third bearing component interchangeable with the first and second bearing components, the third bearing component being adapted to fit between the arms of the second stem; and
    a flange connected to the third bearing component and configured to mate with the slot.

2. A prosthetic joint kit according to claim 1, fuirther comprising an opening in each of the arms, an opening in the second bearing component and a pin adapted to extend through the openings in the arms and second bearing component.

3. A prosthetic joint kit according to claim 1, further comprising an opening in each of the arms, an opening in the third bearing component and a pin adapted to extend through the openings in the arms and the third bearing component.

4. A prosthetic joint kit according to claim 1, wherein the bearing surface of the first bearing component is concave and the second bearing component includes a convex surface.

5. A prosthetic joint kit according to claim 1, wherein the second end of the first stem is wider than the first end of the first stem.

6. A prosthetic joint kit according to claim 1, wherein the second end of the second stem is wider than the first end of the second stem.

7. A prosthetic joint kit according to claim 2, wherein the pin includes a head having a larger diameter than the diameter of the opening in one of the arms.

8. A prosthetic joint kit according to claim 3, wherein the pin includes a head having a larger diameter than the diameter of the opening in one of the arms.

9. A prosthetic elbow kit, comprising:
   an ulnar component having a stem with a first end adapted to fit within the medullary canal of a ulna and a second end;
   a first bearing component adapted to engage the ulnar component;
   a humeral component having a stem with a first end adapted to fit within the medullary canal of a humerus;
   a second bearing component adapted to engage the humeral component and mate with the first bearing component so as to be held in place by the soft tissues of the elbow; and
   a third bearing component interchangeable with the first and second bearing components, the third bearing component adapted to engage the ulnar component and be held in place by the humeral component.

10. A prosthetic elbow kit according to claim 9, wherein the ulnar component includes a slot and the first bearing component includes a flange configured to mate with the slot.

11. A prosthetic elbow kit according to claim 9, wherein the humeral component includes a pair of arms and the second bearing component is adapted to fit between the arms.

12. A prosthetic elbow kit according to claim 11, further comprising an opening formed in each of the arms, an opening formed in the second bearing component and a pin adapted to extend through the openings in the arms and the second bearing component.

13. A prosthetic elbow kit according to claim 9, wherein the humeral component includes a pair of arms and the third bearing component is adapted to fit between the arms.

14. A prosthetic elbow kit according to claim 13, further comprising an opening formed in each of the arms, an opening formed in the third bearing component and a pin adapted to extend through the openings in the arms and the third bearing component.

15. A prosthetic elbow kit according to claim 9, further comprising a slot formed in the ulnar component and a flange connected to the third bearing component and configured to engage the slot.

16. A prosthetic elbow kit according to claim 9, further comprising a slot formed in the ulnar component, a flange connected to the first bearing component and configured to engage the slot, and a flange formed on the third bearing component and configured to engage the slot.

17. A prosthetic elbow kit, comprising:
   a plurality of bearing components, at least one of which is configured for allowing unconstrained prosthetic elbow movement and at least one of which is configured for allowing only constrained prosthetic elbow movement;
   an ulnar component for attachment to a human ulna, the ulnar component having a proximal end and a distal end;
   a humeral component for attachment to a human humerus, the humeral component having a proximal end and a distal end;
   a first bearing mount on the humeral component for engagement with at least two of the plurality of bearing components; and
   a second bearing mount on the ulnar component for engagement with at least two of the plurality of bearing components.

18. The prosthetic elbow kit according to claim 17, wherein the first bearing mount includes a pair of spaced apart arms extending from the humeral component.

19. The prosthetic elbow kit according to claim 17, wherein the first bearing mount is located at the distal end of the humeral component.

20. The prosthetic elbow kit according to claim 17, wherein the second bearing mount is located at the proximal end of the ulnar component.

21. The prosthetic elbow kit according to claim 17, wherein the second bearing mount includes a slot formed in a portion of the ulnar component.

22. The prosthetic elbow kit according to claim 17, wherein the first and second bearing mounts are configured to simultaneously engage one of a plurality of bearing components.

23. A prosthetic elbow kit, comprising:
   a humeral component having a bearing mount;
   an ulnar component having a bearing mount;
   first and second bearing components, the first bearing component configured to engage the ulnar bearing mount and the second bearing component configured to engage the humeral bearing mount and the first bearing component so as to form an unconstrained prosthetic elbow; and
   a third bearing component interchangeable with the first and second bearing components and configured to engage the humeral and ulnar components so as to form a constrained prosthetic elbow.

24. The prosthetic elbow kit according to claim 23, wherein the humeral bearing mount includes a pair of spaced-apart arms.

25. The prosthetic elbow kit according to claim 23, wherein the ulnar bearing mount includes a slot.

26. The prosthetic elbow kit according to claim 23, wherein the third bearing component includes a cylindrical body.

27. The prosthetic elbow kit according to claim 26, wherein the third bearing component further includes an opening.

28. The prosthetic elbow kit according to claim 26, wherein the third bearing component further includes a flange.

29. The prosthetic elbow kit according to claim 28, wherein the flange is configured to mate with the ulnar bearing mount.

30. The prosthetic elbow kit according to claim 23, wherein the first bearing component includes a flange.

31. The prosthetic elbow kit according to claim 30, wherein the flange is configured to mate with the ulnar bearing mount.

32. The prosthetic elbow kit according to claim 23, wherein the humeral bearing mount includes an opening.

33. A prosthetic elbow kit, comprising:

a humeral component;

an ulnar component;

a plurality of bearings for providing pivotal movement of the ulnar component relative to the humeral component in an unconstrained manner, at least one of the bearings being configured to attach to the humeral component and at least one being configured to attach to the ulnar component; and a first bearing, interchangeable with the plurality of bearings, for joining the humeral and ulnar components to form a constrained prosthetic elbow.

\* \* \* \* \*

UNITED STATES PATENT AND TRADEMARK OFFICE
CERTIFICATE OF CORRECTION

PATENT NO.   : 6,027,534
DATED        : February 22, 2000
INVENTOR(S)  : Wack et al.

It is certified that error appears in the above-identified patent and that said Letters Patent is hereby corrected as shown below:

<u>Title page,</u>
The Assignee information should appear as follows, -- DePuy Orthopaedics, Inc., Warsaw, Ind. --.

Signed and Sealed this

Twenty-sixth Day of March, 2002

Attest:

JAMES E. ROGAN
*Attesting Officer*        *Director of the United States Patent and Trademark Office*